United States Patent [19]

Lehmberg et al.

[11] Patent Number: 6,024,991
[45] Date of Patent: *Feb. 15, 2000

[54] TEA CONCENTRATE PREPARED BY ENZYMATIC EXTRACTION AND CONTAINING XANTHAN GUM WHICH IS STABLE AT AMBIENT TEMPERATURE

[75] Inventors: Gregg Lance Lehmberg, Somerset, N.J.; Sheng Xue Ma, Altamonte Springs, Fla.

[73] Assignee: Thomas J. Lipton Co.,, Englewood Cliffs, N.J.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/763,424

[22] Filed: Dec. 11, 1996

Related U.S. Application Data

[60] Provisional application No. 60/020,304, Jun. 19, 1996, and provisional application No. 60/019,986, Jun. 19, 1996.

[51] Int. Cl.⁷ .................................. A23B 7/10; A23F 3/00
[52] U.S. Cl. .......................... 426/52; 426/330.3; 426/435; 426/597
[58] Field of Search ................................ 426/597, 330.3, 426/435, 52

[56] References Cited

U.S. PATENT DOCUMENTS

| | | | |
|---|---|---|---|
| 4,051,267 | 9/1977 | Jongeling | 426/330.3 |
| 4,478,939 | 10/1984 | Adler-Nissen et al. | 435/200 |
| 4,483,876 | 11/1984 | Petersen | 426/52 |
| 4,748,033 | 5/1988 | Syfert et al. | 426/330.3 |
| 4,797,293 | 1/1989 | Evans et al. | 426/597 |
| 5,529,796 | 6/1996 | Gobbo et al. | 426/330.3 |

*Primary Examiner*—Anthony J. Weier
*Attorney, Agent, or Firm*—James J. Farrell

[57] ABSTRACT

A tea concentrate prepared by enzymatic extraction of the tea leaf with a combination of cell wall lysis enzymes and tannase is disclosed where the concentrate is stabilized where necessary by xanthan gum.

3 Claims, 3 Drawing Sheets

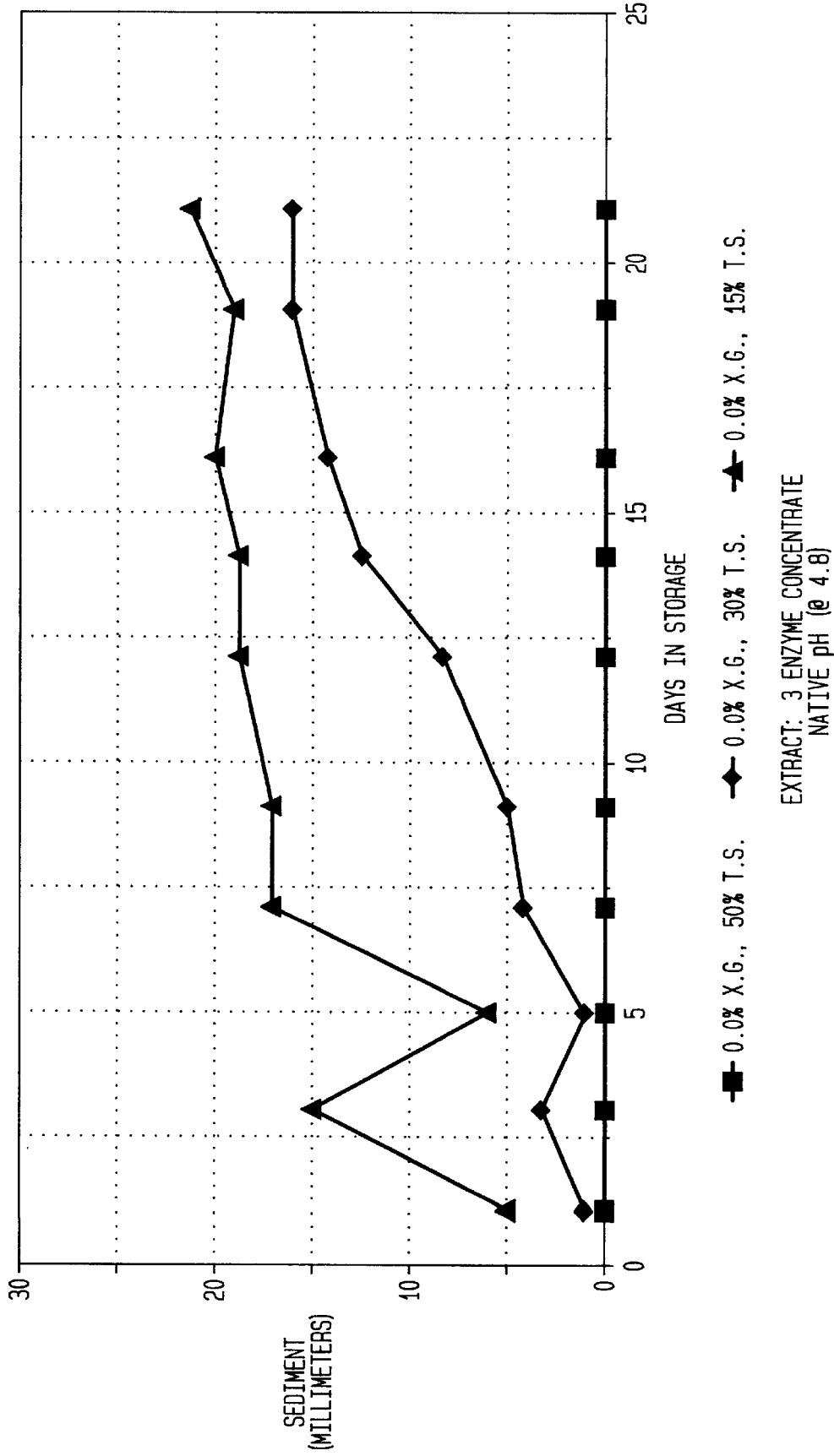

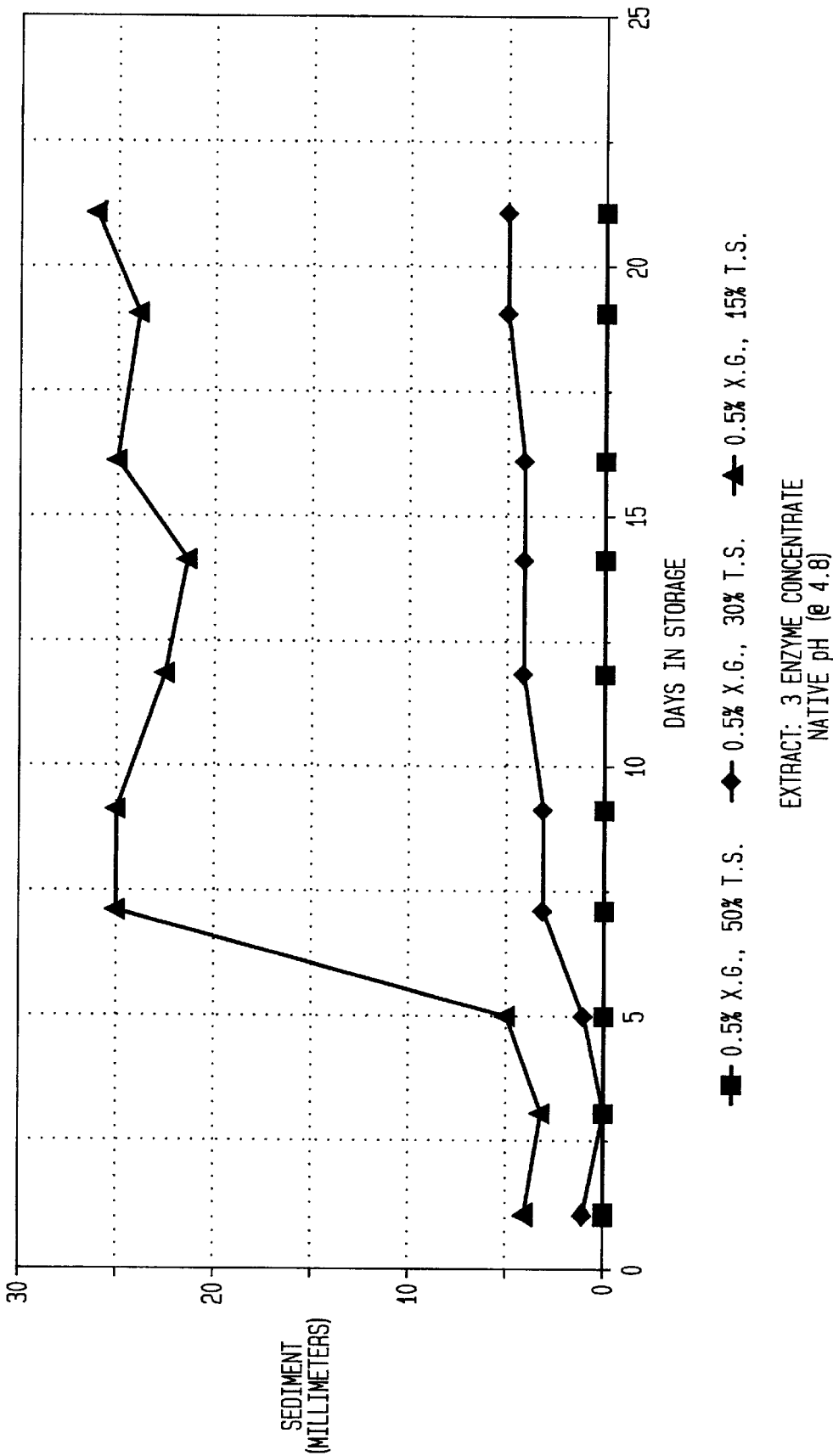

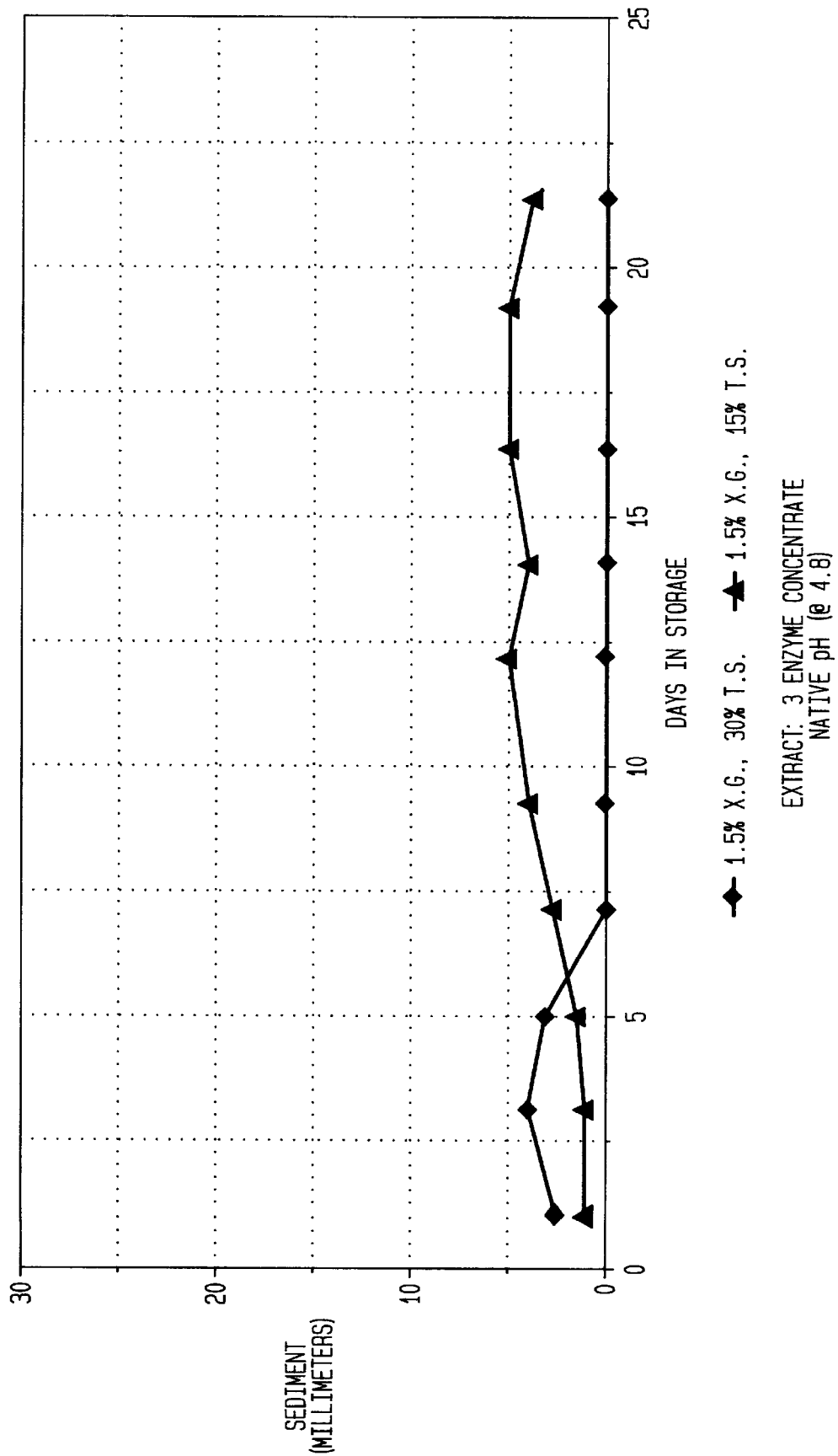

TEA CONCENTRATE PREPARED BY ENZYMATIC EXTRACTION AND CONTAINING XANTHAN GUM WHICH IS STABLE AT AMBIENT TEMPERATURE

CROSS-REFERENCE TO RELATED APPLICATION

This application claims the benefit of U.S. Provisional Application Nos. 60/020,304 filed Jun. 19, 1996 and 60/019,986, filed Jun. 19, 1996.

FIELD OF THE INVENTION

This invention generally relates to tea concentrates having about 20 to about 70% or even higher tea solids.

BACKGROUND OF THE INVENTION

Shelf stable tea concentrates are highly desirable and have several applications. These include: the ability to supply a natural tea concentrate for use in Ready-to-Drink tea and Fountain tea products; as a tea concentrate product for retail sale; and as a preferred method of transporting tea solids. The advantages of a tea concentrate over a powder or a dilute tea extract are that better tea character is obtained. In addition, less energy is employed than for a powder and less weight and volume are needed for shipping a concentrate than for a dilute extract.

In the prior art tea concentrates were considered to be physically unstable, which prevented their use in many tea products. However, it is believed that under certain conditions tea products made from tea concentrates have better quality (e.g., flavor, freshness, etc.) than powders and are more economical than tea powder or dilute tea extract. Therefore, it is highly desirable to have a shelf stable tea concentrate.

The addition of a selected level of high methoxy citrus pectin stabilizes tea products having about 0.1% tea solids and prevents haze and precipitation. This is disclosed in U.S. Pat. No. 5,529,796. However, the same approach to stabilize tea concentrates up to about 40% solids was not successful.

U.S. Pat. No. 4,748,033 disclosed the use of edible gums (xanthan gum, cellulose gums, locust bean gum, sugar gum and mixtures) to prevent flake formation during cyclic freezing and thawing, and to enhance cold water solubility. The solids level for the tea concentrate specified in the patent was 0.4 to 8% (w/w) and the use level of xanthan gum was 5–12% weight of gum to weight of tea solids.

U.S. Pat. No. 4,051,267 to Jongeling disclosed the use of carrageenans for suspending and stabilizing tannins in a tea extract which is transported in a frozen or chilled condition for use in vending machines. However, Jongeling found that the viscosity of the tea extract using xantham gum was so high that the accuracy of dosing in the dispensing machine was impaired.

The use of individual gums or mixtures of gum with selected tea extracts has been disclosed. However, the current invention is very different from the teachings of the prior art. The prior art dealt with much lower levels of tea solids, i.e. 0.4–8%. Further, the prior art did not stabilize tea concentrates containing 20–70% solids. Additionally, the prior art required low temperatures (refrigerated or frozen) to maintain the flavor, clarity, stability and shelf life of the products. Tea concentrates prepared by the current invention in contrast to the art are stable at ambient temperatures. The use level of xanthan in this invention on a tea solids basis is very low 0.5%–2.5%. Lastly, xanthan gum is the most effective out of 14 gums/stabilizers screened including carrageenans and pectins.

Accordingly an object of the invention is to prepare enzymatically extracted tea concentrates at high concentrations which may be stored at ambient temperature for at least six months with good quality. It is believed that this is the first time that tea solids at such high concentrations have been stabilized for extended periods at ambient temperatures.

Yet another object is to provide stable tea concentrate at relatively low pH values as low as about 2.5.

SUMMARY OF THE INVENTION

In order to achieve the goal of shelf stable tea concentrates, a series of natural compounds have been screened and xanthan gum was found to be the most effective. Tea extracts from continuous or batch extraction using specific enzyme treated or extracted tea leaves (i.e., green, black, and oolong tea) were centrifuged. Xanthan gum was added either before or after evaporation and preferably after to achieve a final concentration of 0.5%–2.5% (w/w) on a tea solids basis of the concentrate (20–70%). A high shear force was used to dissolve the gum completely in the concentrate, which is critical to the stability of the final product. The stabilized concentrate was pasteurized, aseptically packed, and stored at ambient temperature. The products made from the concentrate have a fresh brewed tea flavor and good clarity.

Ready-to-Drink (RTD) products prepared from six-month old tea concentrates delivered clear beverages with good organoleptic properties and acceptability even at pH values as low as 2.8. No off-flavor or precipitation was detected in either concentrated or single strength forms.

BRIEF DESCRIPTION OF THE DRAWINGS

FIG. 1 represents a graph of the values reported in Example 2 (15, 30 and 50% tea solids with 0% Xanthan gum).

FIG. 2 represents a graph of the comparative values reported in Example 2 (15, 30 and 50% tea solids with 0.5% Xanthan).

FIG. 3 represents a graph of the comparative values reported in Example 2 (15 and 30% tea solids with 1.5% Xanthan).

DETAILED DESCRIPTION OF THE INVENTION

Black teas, particularly those selected to have a low cream index and which produce highly colored infusions are essentially preferred for the process but, of course, Green and Oolong teas may also be employed if appropriate care is taken.

Particularly preferred are tea concentrates prepared from black tea treated with a combined enzyme system of at least one cell wall digesting enzyme in combination with tannase.

In particular these concentrates are prepared by treating tea leaf with an enzyme cocktail including tannase, and selected cell wall lysis enzymes such as carbohydrases including cellulase and mascerase, for example, Viscozyme™L obtainable from NOVO Industri A/S Denmark. Preferably black tea leaf is used.

The enzymes are fed to a black tea/water slurry in an extractor at low temperature to obtain a tea extract slurry. The enzymes can be combined into a cocktail optionally with appropriate pH adjustment or can be fed to the extractor individually to limit the contact time between the enzymes. The tea extract slurry containing the enzymes is then hot extracted to complete the extraction process and the tea leaf is separated from the tea extract. The tea extract is then preferably pasteurized. This heat treatment deactivates the enzymes.

The separated or decanted tea extract may then be stripped if desired, to collect additional aroma.

The stripped extract is optionally concentrated and then cooled and polished by centrifugation or other clarification methods such as filtration and the like. After polishing the extract is then concentrated preferably by vacuum.

A particularly preferred method of preparing the concentrate is as follows:

About 5 to 20 parts and preferably 5 to 8 parts by weight of water based on the weight of tea leaf is heated to between about 70° F. and 145° F., preferably 120° F. to 140° F. The water is added to the tea leaf and an enzyme mixture consisting of any combination of tannase with cell wall lysis enzymes, for example carbohydrases such as cellulase, pectinase, and mascerase are metered continuously into the extractor. The extractor can be jacketed or insulated to aid in temperature control. The flow of tea leaf, water and enzymes through the extractor is preferably co-current. The length, diameter and flow rates of the system are such that they provide a minimum contact time of at least 20 minutes, preferably at least 60 minutes. The maximum is about 2 to 5 hours or more, depending upon the degree of extraction desired balanced against economics.

The resulting slurry can be separated into extracted tea leaf and extract or be sent on for further batch or continuous higher temperature extraction. The extract is then optionally aroma stripped by conventional means and adjusted to the desired solids level, cooled and centrifuged to remove insoluble material. The extract is then concentrated to about 20% to 70% tea solids preferably about 30% to 65% tea solids.

Enzyme Preparation

The enzyme cocktail is prepared by mixing selected cell wall-digesting enzymes together with enzyme stabilizing agents such as sorbitol and the like in water. Tannase may also be prepared by adding the enzyme to water first but the tannase can also be added as a dry powder. The enzymes are mixed together and their pH is adjusted to about 4 to 10 and preferably 5.5 or above, more preferably to 6 or above so long as the enzyme is not denatured. The cell wall digesting enzyme mixture preferably has its pH adjusted prior to dissolving or adding the tannase into the enzyme cocktail. It is also possible to introduce the enzymes separately into the extractor.

The enzyme batch contains about 340 grams of the cell wall digesting enzymes and contains about 3.8 grams of the tannase on the carrier.

The enzyme cocktail is maintained at a temperature of about 35° F. to 55° F. and is added into the extractor at a rate of about 3.4 g/minute.

The addition of the enzyme solution to the extractor affects the carbohydrate composition, the gallic acid concentration, the acid stability and the cold water solubility and yield. The preferred conditions of the extraction are as follows:

Temperature in the extractor 70° F. to 145° F. and preferably about 120° F. to 140° F.

Enzyme Feed Rate target 3.4 gm./min.

Leaf Feed Rate target 60 lbs./hr.

Water Feed Rate 5.0 to 8.0 lbs./min.

Enzyme Extraction Operation

The tea leaf is fed to the enzyme extractor together with fresh water and enzyme solution. All three components flow co-currently through the extractor. Other methods of delivering appropriate residence time are also acceptable. The extractor is preferably temperature controlled by jacketing or the like.

The enzyme extractor preferably provides about 20 minutes to about 5 or more hours of residence time for the enzyme solution to be in contact with the leaf. Temperature control is important to maximize the effect of the enzymes.

Operating Parameters for the Enzyme Extractor

The following table highlights the preferred operating parameters:

| Operating Parameter | Specification |
| --- | --- |
| Leaf Feed Rate | 60 lb/hr |
| Feedwater Rate | 0.6 to 0.95 gallons/min. |
| Enzyme Feed Rate | 3.4 gm/min |
| Slurry Temp. in Troughs | 120–140° F. |

Extraction

Following the enzyme extraction step, the leaf slurry is fed into a high temperature extractor at a temperature of about 70° F. to 210° F., preferably 100° F. to 190° F. This completes the extraction of the leaf. The ratio of leaf to water in this extraction is about 4 parts to 10 parts water to 1 part leaf.

Pasteurization

If pasteurization is desired, decanted extract from the hot extraction step is pumped at about 2% to 5% tea solids to the Pasteurizer. Pasteurization is accomplished by raising the temperature of the extract to a minimum of about 190° F. The hot extract is then held for about one to ten minutes of residence time to destroy any microorganisms that might be present in the extract. The pasteurization step also denatures the enzymes and stops their activity.

The pasteurized extract is then stripped of aroma if desired and concentrated to the appropriate level for centrifugal polishing.

Polisher Operation

The extract temperature should be about 140° F. or less, preferably about 55° F. to 90° F. The extract is fed to a centrifuge where it is spun for nominally 2 minutes at approximately 8,000 times gravity. The sludge is disposed of and the polished extract retained for concentration. The extract is polished at about 4% to about 10% tea solids.

Preferred Embodiment

In a preferred process of this invention, black tea leaf is mixed with an enzyme cocktail at a weight ratio of from about 0.005 to 0.010 part of enzyme to 1 part of tea leaf preferably 0.007 to 0.008 parts enzyme per part tea leaf. The enzyme solution contains tannase and one or more cell wall lysis enzymes. Preferably, the enzyme solution contains from about 0.5 to 10 units of tannase activity per gram of black tea, from about 2.5 to 5.0 NCU of cellulase, and about 0.33 to 0.66 FBG of carbohydrase per gram of black tea. The tea is extracted with the enzymes at a temperature of from about 70° F. to about 145° F. for from 20 minutes to 5 hours or more. The enzymes are inactivated by heating to a temperature greater than about 150° F. and preferably about 190° F. or above and the tea is then ready for further processing in accordance with the invention.

Enzyme Solution

By "cell wall-digesting enzyme" herein is meant an enzyme or enzymes which breaks down one or more tea cell wall constituents to simpler materials and thus reduces the structural integrity or increases the permeability of the cell wall. Plant cell walls are composed primarily of cellulose, but contain lesser amounts of proteins, hemicellulose, pectins, and lipids. Accordingly, cell wall-digestive enzymes include carbohydrases such as cellulase, hemicellulase, pectinase and dextranase as well as protease, lysozyme and lipases, for example, Novo Industries U.S. Pat. Nos. 4,478,939 and 4,483,876 describe SPS-ase activity.

The tannase, which is used in this invention, is known to hydrolyze galloyl esters. The enzyme is an elaboration product of the growth of certain molds belonging to the genera Aspergillus and Penicillium. *Aspergillus flavus* grown on a medium containing tannic acid as a sole carbon source provides tannase in substantial amounts. Two other specific strains of microorganisms known to produce substantial quantities of tannase are *Aspergillus oryzae*, ATCC No. 9362, and *Aspergillus niger*, ATCC No. 16888. One suitable preparation of tannase enzyme is available commercially from the Enzyme Development Corporation. Yet another is available from Kikkoman. The other cell wall digesting enzymes, such as cellulase, pectinase, and hemicellulase can be obtained from similar commercial enzyme sources. An example of the measurement of tannase activity is given below.

Tannic acid is hydrolyzed in the presence of tannase to gallic acid and a sugar moiety. The hydrolysis of tannic acid results in a reduction of UV absorbance at 310 nm. Tannase activity is therefore determined from the change in absorbance and is defined as the amount of enzyme which hydrolyses 1 micromole of ester bond in tannic acid per minute under the conditions described below.

Reagents and Solutions (1) Citrate Buffer (0.05 M, pH 5.5)

9.6 grams of anhydrous citric acid is dissolved in 800 ml of water. The pH is adjusted with NaOH (50%) to 5.5 and the solution is diluted to 1000 ml with deionized water.

(2) Cell Wall Digesting Enzyme Solution (33.0%)

The solution is a mixture of Viscozyme™L and Celluclast® that have been blended in a ratio of 2:1. This mixture serves as the solvent, stabilizer and blank for the tannase analysis. The solution is prepared on a W/V basis with deionized water. The pH is adjusted with sodium hydroxide to 5.5.

(3) Substrate Solution (Tannic Acid, 0.350% W/V)

The substrate is prepared just before use by dissolving 175 mg of tannic acid in citrate buffer (1) which is then made up to a volume of 50 ml using a volumetric flask.

(4) Ethanol Solution (90%)

100 ml of deionized water is added to a 1000 ml volumetric and the volume is brought to 1000 ml with ethanol.

(5) Tannase Solution (Approx. 2.6–2.9 units/ml.)

The tannase solution is prepared by dissolving 0.1000 grams of tannase in the cell wall digesting enzyme solution (2) W/V to produce a solution that contains 1.000 mg/ml tannase. 1.0 ml of tannase solution is diluted with 18 ml of citrate buffer (1). This brings the tannase into the required activity range for U.S. analysis. The blank is prepared in the same way by mixing 1.0 ml of Novoferm 91 (2) solution with 18 ml of citrate buffer (1).

Stability of Solutions: Citrate buffer (1) when stored at 4° C. is stable as long as no microbial action occurs. The cell wall digesting enzyme solution (2) and substrate solution (3) must be freshly prepared and protected from light. Ethanol solution (4) may be stored at room temperature. Enzyme solution (5) may be stored for several hours at about 0° C.–4° C. after preparation.

Procedure

A. The substrate solution (3) is transferred to a flask and warmed in a water bath at 30° C. for 15 minutes before starting the enzyme reaction.

B. 1.0 ml aliquots of enzyme solution (5) are transferred into test tubes (10 ml). For blank test samples the cell wall digesting enzyme blank solution as specified in (2) is used. All test tubes are warmed in a water bath at 30° C. for 5 minutes before starting the enzyme reaction.

C. The test/reaction is begun by adding 4.0 ml of substrate solution (3) to each test tube (at 30 second intervals) and incubated for 15 minutes at 30° C.

D. The reaction is quenched in flasks for each test sample by adding ethanol solution (4) to each flask. At the end of the reaction time, which should be 15 minutes for each test sample, 952 ul of sample is transferred to the ethanol stop solution and mixed thoroughly. The sample is diluted to volume with additional ethanol solution (4) and mixed.

E. The absorbance of each solution is measured at 310 nm using water as a reference.

Calculations (1) The absorbance measurements that were taken for the samples and blanks are averaged.

(2) Tannase activity may then be calculated from the following equation:

Tannase Activity (Units/gram)=$\Delta A * 150670$

The cell wall digesting enzymes may be cellulase such as Celluclast® 1.5L obtainable from Novo Industries. This material is prepared by fermentation of a selected strain of *Trichoderma reesei*. This cellulase catalyzes the breakdown of cellulose into glucose, cellobiose and higher glucose polymers. Celluclast 1.5 L has 1,500 NCU/g.

One Novo Cellulase Unit (NCU) is the amount of enzyme which, under standard conditions, degrades CMC to reducing carbohydrates with a reduction power corresponding to 1 $\mu$mol glucose per minute.

| Standard Conditions | |
| --- | --- |
| Substrate | CMC (Hercules 7 LFD) |
| Temperature | 40° C. |
| pH | 4.8 |
| Reaction time | 20 minutes |

Another cell wall digesting enzyme is Viscozyme™L obtainable from Novo. Viscozyme 120 L is a multi-enzyme complex containing a wide range of carbohydrases including arabinose, cellulase, β-glucanase, hemicellulase and xylanase. The enzyme also has activity against the branched pectin like substances found in the soy bean cell walls.

The enzyme preparation is produced from a selected strain of the Aspergillus group. The product has an enzyme activity of 120 FBG/ml. (Fungal β Glucanase). The analytical method is available from Novo.

It is found that the pH of the mixed enzyme solution is very important in obtaining the highest yields of gallic acid as a result of high tannase activity. The combination of cell wall digesting enzymes has a pH of about 4.0 to 5.0 and this is adjusted up to 10 and preferably to 5.0 to 6.5 to provide higher tannase activity.

Once the polished tea extract has been prepared by the enzymatic treatment of the invention it is then concentrated by means well known in the art. Preferably the concentrates are prepared by evaporation under vacuum. The preferred conditions if evaporation is used are a temperature of about 115° F. to 195° F. and a pressure of about 1.5 psia to about 10 psia. In this way the extract can be concentrated without having a negative impact on the organoleptic properties of the tea. A commercial concentration rising or falling film evaporator is usually employed. Once the tea is concentrated to a level of about 20% to about 70% tea solids a selected amount of xantham gum is then added to stabilize the concentrate. The gum is preferably prepared as a solution then added to the tea concentrate under relatively high shear to insure homogeneous dispersion. However, this gum can also be added as a powder.

The tea extract can be concentrated to any level which is still fluid enough to be workable but levels of about 20% to about 70% and preferably about 30% to about 65% are preferred for ease of handling.

As used herein, the terms "tea concentrate" refers to a product derived from concentrated tea extract which is diluted with water to form a drinkable tea beverage. Tea concentrates of the present invention comprise from about 20 to about 70% tea solids. Preferred tea concentrates of the present invention comprise from abut 30 to about 65% by weight tea solids. The tea concentrates of the present invention are in liquid product form.

As used herein, the term "tea beverage" refers to a drinkable beverage prepared from the tea concentrates of the present invention by dilution with water. The tea concentrates of the present invention are generally diluted with sufficient water to provide the tea beverage. Preferred tea concentrates are typically diluted to a minimum of about 0.08% tea solids to provide the tea beverage.

As used herein, the term "tea solids" refer to those solids normally present in a tea extract. Polyphenolic compounds are normally the primary component of tea solids. However, tea solids can also include caffeine, proteins, amino acids, minerals and carbohydrates.

Xanthan gum is a biopolymer available from Kelco, a division of Merck and Company as Keltrol® and Keltrol®RD. The amount of xanthan that can be used varies from about 0.5% up to about 2.5% based on the total amount of tea solids present. The maximum amount of xanthan is limited at higher levels of tea solids because of viscosity increases which render the concentrate too viscous to handle easily. At lower concentrations of tea solids higher amounts of xanthan could be used but are not necessary and would be economically undesirable.

All parts percentages and proportions herein are by weight unless otherwise specified.

EXAMPLE 1

Fourteen different food-grade additives or stabilizers were selected for evaluation in an initial screening study reported in Table 1 below. The results were observed visually and general comments are reported. Two to three different concentrations for each additive/stabilizer were tested in tea concentrates prepared as described above. The additive/stabilizer was added slowly into 150 ml of tea concentrate in an 8 oz. glass jar and mixed with a high speed homogenizer (Polytron) for 1–3 minutes to assure that the additive/stabilizer was in solution. The control product was prepared in the same way but without additive/stabilizer. All concentrates were pasteurized in 8 oz. jars using a 600 watt microwave oven at full power for 50 seconds/bottle. This process was sufficient to heat the product to 190°–200° F. The jars were capped immediately and inverted for 1 minute to sterilize the cap. Samples were stored at ambient temperature.

Xanthan gum was found to be the most effective additive/stabilizer among the 14 compounds screened at stabilizing tea concentrates. For tea concentrates extracted with the enzyme mixture of the invention and containing 35% or higher solids, xanthan gum did not contribute additional benefits to the physical stability. Xanthan gum at levels above about 1.5% (w/w) resulted in viscosities that were too high to maintain the flowability of the concentrate when its solids levels were above about 35%.

When the solids concentration was lower than about 35%, xanthan gum was very effective in stabilizing the concentrates. The levels of xanthan gum needed were inversely proportional to the solids level of tea concentrates. For example, at 20% solids level, 2.5% (w/w) of xanthan gum was needed to stabilize the concentrates while at the 30% solids level, only 1.0% (w/w) of xanthan gum is needed. The results from this study suggested that xanthan gum at levels of 0–2.5% (w/w) is sufficient to stabilize tea concentrates at solids levels ranging from 20–70%. The xanthan gum level needed was determined by the tea solids concentration of the tea concentrate.

TABLE 1

Additives/Stabilizers Screened For Stabilizing Liquid Tea Concentrates

| Additives/Stabilizer | Use Level (%, w/v) | Characteristics |
| --- | --- | --- |
| Pectin | 2.0%, 3.0%, 4.0% | High methoxy citrus pectin |
| Mexpectin RS 461 | 2.0%, 3.0%, 4.0% | High methoxy citrus pectin from another source |
| Mexpectin HV 465 | 2.0%, 3.0%, 4.0% | High methoxy citrus pectin (purer) |
| Citrus Pectin | 2.0%, 3.0%, 4.0% | Low methoxy citrus pectin from another source |
| Gum Arabic | 3.0%, 4.0%, 5.0% | Used in flavored tea (tea agglomeration) |
| Neuture | 3.0%, 4.0% | A polysaccharide |
| Carrageenan Km-1 | 0.5%, 1.0%, 2.0% | Seaweed for increased viscosity |
| Carrageenan k-100 | 0.5%, 1.0%, 2.0% | Seaweed with different purity |
| Ethanol | 5%, 10%, 15%, 20% | ≦5% was beneficial to clarity but did not prevent precipitation |
| Dariloid 400 | 0.1%, 0.25%, 0.5% | Mixture of various gum (xanthan gum) |
| Gellan Gel F | 0.1%, 0.25%, 0.5% | Low viscosity with high shear force during cooling process |

TABLE 1-continued

Additives/Stabilizers Screened For Stabilizing Liquid Tea Concentrates

| Additives/Stabilizer | Use Level (%, w/v) | Characteristics |
|---|---|---|
| Gellan Gum K3B418 | 0.1%, 0.25%, 0.5% | Citrate salt of native gel F for flavor solubility improvements |
| Keltrol | 0.1%, 0.25%, 0.5% | Xanthan gum, increase viscosity significantly |
| Keltrol RD | 0.1%, 0.25%, 0.5% | Ready disperse form of xanthan gum, much clearer, less color |

EXAMPLE 2

The solids level of the tea concentrates examined ranged from 0.72%–50%. All tea solids concentrations were run with 0% Xanthan gum (XG) and 0.5% w/w Xanthan gum; 1.5% XG and 4.5% XG were run at all solids concentrations except 50%. 4.5% Xanthan gum at a 30% tea solids level was too viscous to handle easily. Lower tea solids concentrations were obtained by diluting the 50% concentrate with deionized water. The products were pasteurized prior to dilution using microwave energy and stored at ambient conditions.

The results indicated that tea concentrates produced from leaf treated with Tannase, Celluclast and Viscozyme and solids concentrations about 35% or higher were stable without Xanthan gum and below about 35%, the stability began to deteriorate. At solids concentrations lower than 35%, the use of xanthan gum at 0.5% w/w to 2.5% w/w greatly improved the stability compared to control (no xanthan). It is surprising and encouraging that higher solids concentrations are more stable because tea concentrates at higher solids concentration are more desirable than lower solids due to reduced volumes of handling and transportation and better microbiological stability.

The results reported in Table 2 confirmed the initial observations. Generally, tea concentrates of the invention with solids concentrations equal to or greater than 35% (w/w) had better physical stability than those below 35%. The use of 0.5% w/w xanthan gum did not influence the physical stability of tea concentrates at or above 35% solids. However, xanthan gum at 0.5% w/w did improve the physical stability of the concentrates whose solids levels were lower than 35%. Higher amounts of Xanthan gum up to 2.5% w/w may be necessary to completely stabilize the concentrates in the range of 20% to 35% solids.

The test solutions were prepared first by preparing a concentrate then adding a 3% Xanthan gum solution to a predetermined level to the concentrate and mixing. The concentrate was then pasteurized. Lower concentrations were prepared by dilution with hot deionized water.

The dilutions were placed in a centrifuge tube with a nominal capacity of 200 ml, obtained from the Nalge® Company. The tube had a diameter of 61.5 mm and a length of 126.5 mm. The tube had a conical bottom holding about 50 ml. The amount of sediment in the bottom after selected periods of time can be observed visually. The physical stability of the products was scored based on the degree of precipitation at the bottom of the bottle. The evaluation criteria for stable tea concentrates was that they have less than 1 mm of precipitate or preferably are substantially free of precipitate at the bottom.

The numerical results of tests are reported in Table 2 below.

TABLE 2

| DAY # | 1 | 3 | 5 | 7 | 9 | 12 | 14 | 16 | 19 | 21 |
|---|---|---|---|---|---|---|---|---|---|---|
| % Solids | | | | SEDIMENT MILLIMETER | | | | | | |
| 0.0% Xanthan | | | | | | | | | | |
| 50.00% | 0 | 0 | 0 | 0 | 0 | 0 | 0 | 0 | 0 | 0 |
| 30.00% | 1 | 3 | 1 | 4 | 5 | 8 | 12 | 14 | 16 | 16 |
| 15.00% | 5 | 15 | 6 | 17 | 17 | 19 | 19 | 20 | 19 | 21 |
| 6.00% | 3 | 3 | 4 | 8 | 8 | 9 | 9 | 9 | 9 | 9 |
| 2.10% | 0 | 0 | 3 | 0 | 0 | 0 | 0 | 0 | 0 | 0 |
| 0.72% | 0 | 0 | 0 | 0 | 0 | 0 | 0 | 0 | 0 | 0 |
| 0.5% Xanthan | | | | SEDIMENT MILLIMETER | | | | | | |
| 50.00% | 0 | 0 | 0 | 0 | 0 | 0 | 0 | 0 | 0 | 0 |
| 30.00% | 1 | 0 | 1 | 3 | 3 | 4 | 4 | 4 | 5 | 5 |
| 15.00% | 4 | 3 | 5 | 25 | 25 | 23 | 22 | 25 | 24 | 26 |
| 6.00% | 3 | 3 | 4 | 10 | 11 | 12 | 12 | 13 | 13 | 14 |
| 2.10% | 1.0 | 1 | 3 | 2 | 2 | 3 | 3 | 4 | 4 | 4 |
| 0.72% | 0 | 0 | 0 | 0 | 0 | 0 | 0 | 0 | 0 | 0 |
| 1.5% Xanthan | | | | SEDIMENT MILLIMETER | | | | | | |
| 30.00% | 2 | 4 | 3 | 0 | 0 | 0 | 0 | 0 | 0 | 0 |
| 15.00% | 1 | 1 | 2 | 3 | 4 | 5 | 4 | 5 | 5 | 4 |
| 6.00% | 6 | 2 | 7 | 10 | 10 | 11 | 10 | 12 | 13 | 13 |
| 2.10% | 3 | 1 | 1 | 3 | 4 | 5 | 4 | 5 | 5 | 4 |
| 0.72% | 2 | 0 | 0 | 0 | 0 | 0 | 0 | 0 | 0 | 0 |
| 4.5% Xanthan | | | | SEDIMENT MILLIMETER | | | | | | |
| 30.00% | 0 | 0 | 0 | 0 | 0 | 0 | 0 | 0 | 0 | 0 |
| 15.00% | 2 | 3 | 3 | 3 | 3 | 3 | 4 | 5 | 4 | 4 |
| 6.00% | 0 | 0 | 2 | 2 | 3 | 4 | 4 | 3 | 3 | 3 |
| 2.10% | 4 | 0 | 2 | 17 | 18 | 25 | 26 | 26 | 27 | 28 |
| 0.72% | 1 | 0 | 2 | 0 | 0 | 0 | 0 | 0 | 0 | 0 |

Although the invention has been described in detail with respect to preferred embodiments thereof, variations and modifications will be readily apparent to those skilled in the art without departing from the spirit and scope of the invention as set forth in the claims.

What is claimed is:

1. An aqueous tea concentrate prepared by enzymatic extraction wherein at least one enzyme is tannase and having a physical stability of less than 1 mm of precipitate when stored at ambient temperature for at least six months when the amount of tea solids is from about 20% to about 70% and when the tea solids concentration is less than about 35% said tea concentrate contains a sole gum in an amount of about 0.5 to about 2.5% xanthan gum on the basis of weight of the gum to weight of the tea solids and wherein the amount of xanthan gum is proportional to the amount of tea solids.

2. An aqueous tea concentrate as defined in claim 1 having a pH of about 2.5 to about 5.5.

3. An aqueous tea concentrate prepared by enzymatic extraction wherein at least one enzyme is tannase, said concentrate having at least about 50% tea solids and being stable with substantially no precipitate for at least about six months at ambient temperature.

* * * * *